United States Patent [19]

Dosako et al.

[11] Patent Number: 5,017,559

[45] Date of Patent: May 21, 1991

[54] AGENT FOR BLOCKING NONSPECIFIC ADSORPTION, PROCESS FOR PREPARING THEREOF AND METHOD OF BLOCKING NONSPECIFIC ADSORPTION

[75] Inventors: Shunichi Dosako, Saitamaken; Hiroshi Shinmoto, Kawagoeshi, both of Japan

[73] Assignee: Snow Brand Milk Products Co., Ltd., Sapporo, Japan

[21] Appl. No.: 314,897

[22] Filed: Feb. 24, 1989

[30] Foreign Application Priority Data

Feb. 26, 1988 [JP] Japan .................................. 63-42154
Jul. 27, 1988 [JP] Japan ................................. 63-185521

[51] Int. Cl.$^5$ .............................................. A61K 37/16
[52] U.S. Cl. ..................................... 514/21; 530/360; 530/833; 530/360
[58] Field of Search ................... 514/21; 530/360, 833

[56] References Cited

U.S. PATENT DOCUMENTS 4,692,338  9/1987  Irvine et al. ........................ 426/583

OTHER PUBLICATIONS

Robertson, J. of Immunological Methods; vol. 76, No. 1, 1985 pp. 195–196.
Johnson, Gene Anal. Techn. 1:3–8 (1984).

Primary Examiner—Howard E. Schain
Assistant Examiner—Choon Koh
Attorney, Agent, or Firm—Fleit, Jacobson, Cohn, Price, Holman & Stern

[57] ABSTRACT

The present invention provides an agent utilizing for immunological assays in medical fields for blocking nonspecific adsorption, a process for preparing thereof and a method of blocking nonspecific adsorption. The agent contains a combination of milk protein as an effective constituent and a buffer solution containing one or more principal constituents selected from the group of organic acids and their salts.

9 Claims, 2 Drawing Sheets 5,017,559

AGENT FOR BLOCKING NONSPECIFIC ADSORPTION, PROCESS FOR PREPARING THEREOF AND METHOD OF BLOCKING NONSPECIFIC ADSORPTION

BACKGROUND OF THE INVENTION

The present invention relates to an agent which is utilized for immunological assays in medical fields for blocking nonspecific adsorption, a process for preparing thereof and a method of blocking nonspecific adsorption.

In recent years, immunological techniques such as enzyme-linked immunosorbent assay (ELISA), radioimmunoassay (RIA), Western blot technique and the like are often utilized in the fields of clinical tests, immunology, biochemistry, molecular biology and the like.

In these techniques, the desired material is fixed and assayed by fixing the object material to a solid phase such as a plate, a nitrocellulose membrane, etc., by adding an isotope or an enzyme-labelled antibody (a probe) which binds specifically to the material and then by determining its radiation level or enzyme activity. Then, it is important that the probe reacts with the object material alone and the probe can not adsorb specifically to the solid phase.

Therefore, after fixing the object material to the solid phase, the absorbing point on the solid phase must be closed by adding a blocking agent (an agent for blocking nonspecific adsorption). As an example, in the case of ELISA, the blocking agent is added after antigen is fixed to the plate, and then the probe is added. The blocking agent serves to prevent nonspecific adsorption of the probe to the plate.

Usually, a solution of bovine serum albumin (BSA) is used as the blocking agent. It needs to dissolve BSA in concentration more than 1% generally, and in concentration more than 2%, preferably about 5% for perfectly blocking nonspecific adsorption. BSA is a protein which is easily available in relatively large amount. However, BSA contributes to the high cost of analysis because it takes long time for dissolving BSA in the solution and because its price is high.

However, any material, which has no mutual interaction against the object material or a probe and can adsorb well to a solid phase, can act as a blocking agent theoretically. Accordingly, it is desired to develop an inexpensive and excellent blocking agent.

In 1984, Johnson et al reported that nonfat dry milk (SMP) was superior to BSA for blocking nonspecific adsorption in Southern blot analyses, and a 5% SMP solution acted as an efficient blocking agent in ELISA (Gene Anal. Techn. Vol. 1. pp. 3–8, 1984). Further, Miskimins et al reported that a 5% SMP solution could be an efficient blocking agent (Proc. Natl. Acad. Sci. U.S.A. Vol. 82. pp. 6741–6744, October 1985). Then, Ohta described the efficiency of SMP in the introduction of cloning technology in which expressed vector λgt11 was used (Saibo Kogaku, Vol. 5, No. 3, pp264–270, 1986).

In the above publications, SMP is used as a blocking agent which is dissolved in Tris buffer solution. If the solution of SMP is used as it is, its merchandise value for a reagent is remarkably lowered by the milky turbidity of the solution. When the blocking agent is mass-produced and is on the market as merchandise, it is more advantageous under normal temperature conditions than in low temperature conditions in the cost-effectiveness. In the normal temperature conditions, the SMP solution should be sterilized by an autoclave and the like. However, when SMP was merely dissolved in water or a buffer solution of Tris or phosphate, it was found that its merchandise value was lost because the solution was browned by heating, the turbidity of the solution was increased and a precipitate was ocationally produced from the solution.

SUMMARY OF THE INVENTION

The first object of the present invention is to provide a liquid agent for blocking nonspecific adsorption having transparency, which is able to sterilize without discoloring and is very excellent in the blocking effect.

Further, after breaking the seal, the liquid agent for blocking nonspecific adsorption should be used as soon as possible, or preserved by freezing. Moreover, the disadvantage is the high cost of transportation. Then, an agent for blocking nonspecific adsorption which is powder and utilizable only by dissolving a certain volume into deionized water is desired.

The most simple process for producing the powder agent for blocking nonspecific adsorption comprises that powdered raw materials are mixed as it is. In this case, buffer easily dissolves in cold water, but the solubility of the milk protein is not good. In the other case, in the process comprising that the liquid agent for blocking nonspecific adsorption is dried after concentrating, it is found that a precipitate is produced when a certain concentration of the liquid is obtained.

Accordingly, the second object of the present invention is to provide a process for preparing a powder agent for blocking nonspecific adsorption, the agent can easily dissolve in cold water, it is very excellent in the blocking effect for nonspecific adsorption and it has the same blocking ability as that of the above sterilized liquid agent for blocking nonspecific adsorption.

The present invention resides in a liquid or powder agent for blocking nonspecific adsorption which can be obtained at a low price and preserved at normal temperature for a long time, in which the agent contains a combination of milk protein as an effective constituent and a buffer solution containing one or more principal constituents selected from the group of organic acids and their salts.

DETAILED DESCRIPTION OF THE INVENTION

Figure 1A:
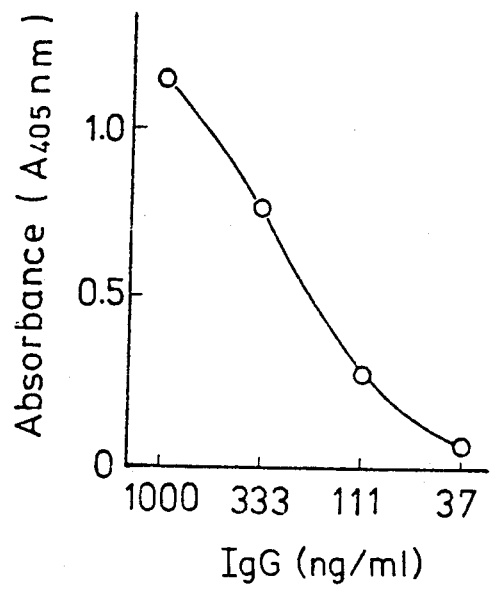
FIG. 1 is a graph showing standard curves of ELISA of human IgG in cases of using of 2% BSA/PBS (A) and 1% SMP/0.1M sodium citrate (pH6.2) (B) as the agents for blocking nonspecific adsorption in Example 2.

The milk protein used in the present invention can be utilized by combining with one or more materials selected from the group of casein, whey protein concentrate (WPC), nonfat dry milk and skim milk. When WPC is combined, the concentration less than 50% in the milk solid is desirable. When WPC is combined in concentration more than 50%, it sometimes precipitates after heating. The milk protein can be restrictively decomposed with protease, but the decomposition must be conducted partially because highly decomposed protein becomes unstable on sterilization.

The principal constituents of the buffer to be used in the present invention are one or more compounds selected from the group of organic acids such as citric acid, maleic acid, malic acid, succinic acid, malonic acid and the like, and their salts.

The production of the liquid agent for blocking nonspecific adsorption of the present invention is that milk protein as an effective constituent and a buffer solution containing one or more principal constituents selected from the group of organic acids and their salts are combined.

The production of the powder agent for blocking nonspecific adsorption of the present invention is that a solution (A) which dissolves 10–40% of milk raw materials containing the milk protein as the effective constituent in the buffer solution containing 0.1–0.3 mole of one or more principal constituents selected from the group of organic acids and their salts is dried to powder, and a buffer solution (B) which contains one or more principal constituents selected from the group of organic acids and their salts is dried to powder, respectively, and the A powder and the B powder are mixed.

The pH of the buffer is preferably in the range from 5.3 to 7.0. As the effective constituents are difficult to dissolve in the buffer having the pH of less than 5.3, the pH is adjusted to 5.3 and more, preferably 5.5 and more. The upper limit of the pH is preferably 7.0, and more preferably 6.5 and less. When the pH is above 7, the buffer capacity of the organic acid become less, and the product is remarkably browned by sterilizing treatment.

The pH is controlled by adding a solution of alkali such as sodium hydroxide or potassium hydroxide, a solution of acid such as hydrochloric acid, sulfuric acid, acetic acid, or one or more combinations of the said organic acids and their salts.

In case of the liquid agent for blocking nonspecific adsorption, the ratio of milk solid concentration(%)/organic acid concentration(mM) is preferably 0.1 and less, more preferably 0.02 and less. When the ratio is 0.1 and more, e.g. 0.2, transparent product is obtained by sterilizing but the products are browned. For example, when the ratio is 2.0, the transparency of the product is lost.

After preparing the effective constituents under the above conditions, the product can be sterilized. The sterilize conditions are obtained usually in an autoclave by heating, e.g. at 121° C. for ten minutes. In addition, the sterilize conditions are obtained by the same heating conditions as that of the production of long-lived drinks, e.g. at 140°–150° C. for 2–4 seconds.

In case of the powder agent for blocking nonspecific adsorption, the raw materials which contain principal constituents of milk protein for dissolving in the buffer are prepared in an amount from 10% to 40% by weight converted to a dry basis. When the amount is not over 10% by weight, the drying efficiency is not good. When the amount is over 40% by weight, it becomes difficult to dissolve the materials. Most preferable amount is in the range from 20% to 30% by weight.

The concentration of the organic acids or their salts in the buffer solution which dissolves the raw material containing the milk protein as the principal constituents is in the range from 0.1 mole to 0.3 mole. When the concentration is not over 0.1 mole, the milk protein constituents are difficult to dissolve in cold water, and when the concentration is over 0.3 mole, a precipitate is observed.

The drying can be conducted by freeze-drying, spray drying and the like, and though it is not limited especially, the spray drying is preferable by considering the production cost. The drying conditions are not limited especially, and usual conditions such as at the blow temperature of 180° C. and at the nozzle exit temperature of 96° C. can be given. As the dried powder (abbreviated as the A powder) itself is dissolved in deionized water in an amount of above 0.1% by weight of the milk protein constituent, the obtained solution exerts very excellent blocking effect for nonspecific adsorption. However, it is found that the color development of enzyme-substrate reaction is significantly limited in the enzyme-linked immunosorbent assay (ELISA) as shown in Table 1. This is because the concentration of organic acids or their salts is low. The powder which contains principal constituents selected from the insufficient organic acids or their salts should be specially prepared (The powder is abbreviated as the B powder). The organic acids and their salts may be combined at a fixed pH, or the organic acids and strong bases may be combined at a fixed pH. When the mixture of the A powder and the B powder is dissolved in water in an amount of 0.1% to 10% by weight, the pH value is 5.3–7.0.

The mixture ratio of the A powder and the B powder in water is represented by the following formula:

$$\text{milk solid concentration (\%)/concentration converted in terms of organic acid (mM)} \leq 0.1$$

(in the formula, the concentration converted in terms of organic acid $\leq 500$ mM)

Further, lactose, starch, common salt and the like may be added to the B powder.

After the A powder and the B powder are mixed, the mixture is dissolved in water in a fixed concentration and sterilized. There is no problem in this process.

Moreover, the method of blocking nonspecific adsorption of the present invention is characterized that the method comprises using a solution which contains a combination of milk protein as an effective constituent and a buffer solution containing at least one compound selected from the group of organic acids and their salts as a principal constituent.

According to the present invention, the agent for blocking nonspecific adsorption can be provided instead of conventional BSA, and the agent has transparency and is obtained at a low cost and sterilized without discoloring. Further, these agents give very excellent blocking effect in immunological assays. Moreover, these agents can be on the market under normal temperature conditions. The merit is that the agent is easily handled.

DESCRIPTION OF THE PREFERRED EMBODIMENTS

The following Examples illustrate the present invention more specifically, but these will not always be precise in practical applications.

EXAMPLE 1

Nonspecific Adsorption of an Enzyme-Labelled Antibody on an ELISA Plate Having 96 Wells In each ELISA plate having 96 wells (produced by Sumitomo Bakelite Company), an agent for blocking nonspecific adsorption is pipetted in an amount of 400 μl per well, the plate was left at room temperature for one hour and blocked. Then, peroxidase-labelled anti-human IgG (prepared by Tago Company) was diluted to 1,000 times with the agent for blocking nonspecific adsorption, and the diluted solution was pipetted in an amount of 50 μl per well.

After the plate was left at room temperature for one hour, the plate was washed with phosphate buffered saline containing 0.05% Tween 20 (PBS-Tween) for six times, and ABTS (2,2'-azinobis-(3-ethylbenzothiazolin-6-sulfonic acid)) as a substrate was added to each well. After ten minutes, the absorbance was determined at 405 nm with Titertek multiskan (produced by Flow Laboratory Company). The determination was continuously carried out for three times.

As the agent for blocking nonspecific adsorption, the following solutions were used; a solution which was obtained by dissolving 2% BSA in PBS and diluting the BSA solution to prescribed concentration with deionized water, and a solution which was obtained by dissolving SMP in 1% concentration with 0.1M citric acid adjusted to pH6.2 with sodium hydroxide, heating the SMP solution in an autoclave at 121° C. for ten minutes, and diluting the SMP solution within prescribed concentration with deionized water. The results are shown in Table 1.

When the agent for blocking nonspecific adsorption was not used, very high nonspecific adsorption was exhibited. However, when BSA was used, the nonspecific adsorption was blocked in concentration above 1.0% in the range of experimental errors.

The other hand, when SMP was used, the nonspecific adsorption was blocked even if SMP was diluted to 0.0625% and citric acid was diluted to 6.25 mM.

TABLE 1

| Blocking agent | Dilution | Absorbance (A405 nm ± SD) |
| --- | --- | --- |
| PBS | | 1.422 ± 0.048 |
| 2% BSA/PBS | 1 | 0.004 ± 0.003 |
| | ½ | 0.005 ± 0.007 |
| | ¼ | 0.026 ± 0.007 |
| | ⅛ | 0.084 ± 0.038 |
| | 1/16 | 0.146 ± 0.020 |
| 1% SMP/ 0.1M citric acid | 1 | 0 ± 0 |
| | ½ | 0 ± 0 |
| | ¼ | 0 ± 0 |
| | ⅛ | 0 ± 0 |
| | 1/10 | 0 ± 0 |
| | 1/16 | 0 ± 0 |
| | 1/100 | 0.189 ± 0.017 |

(In this TABLE, BSA was not sterilized.)

EXAMPLE 2

Embodiment of ELISA

A mixed solution 50 μl of anti-human κ and anti-human λIgG (prepared by Tago Company) which was diluted to 1,000 times with 0.05M sodium bicarbonate solution was injected in each well of an ELISA plate having 96 holes (produced by Sumitomo Bakelite Company), and the plate was allowed to stand overnight at 4° C. The next morning, the antibody solution was discarded, and an agent for blocking nonspecific adsorption was charged into each well and left for one hour. After each well was washed with PBS-Tween for two times, each 50 μl of human serum IgG (prepared by Midori Juji Company) having concentrations of 0–1000 ng/ml was added and left for one hour. After each well was washed with PBS-Tween for six times, ABTS was added and the absorbance was determined at 405 nm.

As the agent for blocking nonspecific adsorption, and a solution which was obtained by treating 2% BSA/PBS and 1% SMP/0.1M citric acid-Na (pH6.2) shown in Example 1 in an autoclave and diluting the resulting material with deionized water to ten times was used.

Figure 1B:
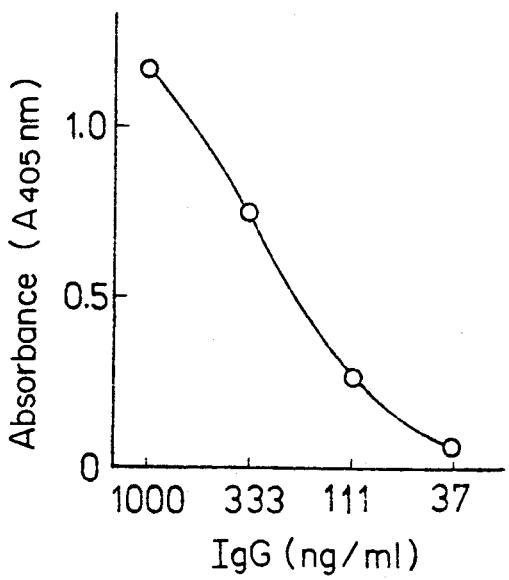

The results are shown in FIG. 1, and no difference was observed between (A) and (B).

EXAMPLE 3

Degree of Browning After Sterilizing

After dissolving 1% SMP in each buffer solution (pH6.1), the solution was treated with an autoclave at 121° C. for ten minutes, and their turbidity, the presence of precipitates and their degree of browning were judged with the naked eye.

As shown in Table 2, when citric acid, maleic acid, succinic acid, malic acid or malonic acid was used, buffers were transparent, no precipitate was observed, and no browning was observed.

TABLE 2

Turbidity, precipitates and degree of browning after sterilizing 1% SMP in each buffer solution

| Buffer | Turbidity | Precipitate | Degree of Browning |
| --- | --- | --- | --- |
| Water | +++ | − | ++ |
| PBS(pH 7.2) | + | ++ | +++ |
| 1M Tris-HCl(pH 7.4) | ++ | ++ | +++ |
| Water + 0.1% EDTA(pH 6.0) | + | + | − |
| 0.2M citric acid —NaOH(pH 6.0) | − | − | − |
| 0.2M citric acid —NaOH(pH 6.0) | − | − | − |
| 0.2M acetic acid —NaOH(pH 6.0) | ++ | ++ | + |
| 0.2M oxalic acid —NaOH(pH 6.0) | +++ | − | ++ |
| 0.2M maleic acid —NaOH(pH 6.0) | − | − | − |
| 0.2M succinic acid —NaOH(pH 6.0) | − | − | − |
| 0.2M malic acid —NaOH(pH 6.0) | − | − | ± |
| 0.2M tartaric acid —NaOH(pH 6.0) | +++ | − | +++ |
| 0.2M malonic acid —NaOH(pH 6.0) | − | − | − |
| 0.2M propionic acid —NaOH(pH 6.0) | +++ | + | ++ |

EXAMPLE 4

Kinds of Milk Protein and the Brocking Effect

The following agents for blocking nonspecific adsorption were prepared.
(1) 1% BSA/PBS (pH7.2)
(2) 1% Nonfat dry milk/50 mM citric acid + 50 mM maleic acid (pH6.3)
(3) 0.5% Casein/100 mM maleic acid (pH6.1)
(4) 0.7% Casein + 0.3% WPC/100 mM citric acid (pH6.2)

(5) 0.5% Nonfat dry milk+0.5% casein/50 mM maleic acid+50 mM malonic acid (pH6.1).

The agents of (2)-(5) were indirectly sterilized at 140° C. for two seconds.

The same test of blocking effect as in Example 1 was conducted except that peroxidase-labelled anti-mouse IgG (prepared by Tago Company) was used instead of the peroxidase-labelled anti-human IgG. Further, after ABTS was added and allowed to stand at room temperature for 15 minutes, the absorbance was determined at 405 nm. The results are shown in Table 3.

TABLE 3

| Blocking agent | Absorbance (A405 nm ± SD) |
| --- | --- |
| PBS | 1.492 ± 0.048 |
| (1) | 0.011 ± 0.008 |
| (2) | 0.000 ± 0.000 |
| (3) | 0.002 ± 0.001 |
| (4) | 0.004 ± 0.002 |
| (5) | 0.000 ± 0.000 |

When the milk protein was used, the background was low and more excellent effect was exerted than that of BSA. In this case, (4) which was blended with WPC exerted less blocking effect, but there was no problems in practice.

EXAMPLE 5

Production of the Powder Agent for Blocking Nonspecific Adsorption

To ten liters of 0.2 mole of maleic acid-sodium hydroxide (pH6.1), sodium caseinate was dissolved in an amount of 15% by weight. The solution was spray-dried at a blow temperature of 160° C. and at a nozzle exit temperature of 90° C., and 1.2 kg of powder was obtained. Then, maleic acid and sodium hydroxide are mixed at the weight ratio of 5:3 and ground to a powder. 1.15 kg of the former powder and 1.6 kg of the latter powder were mixed, and the powder agent for blocking nonspecific adsorption was prepared.

EXAMPLE 6

Production of the Powder Agent for Blocking Nonspecific Adsorption

To ten liters of water, 384 g of citric anhydride and 718 ml of a solution containing sodium hydroxide in an amount of 25% by weight were dissolved. The pH was 6.2. Two kg of non fat dry milk was dissolved to the solution, the resulting solution was spray-dried at a blow temperature of 180° C. and at a nozzle exit temperature of 95° C., and two kg of powder was obtained. Then, 57.5 g of anhhydrous citric acid, 1.235 kg of sodium citrate (two hydrate) and 67 g of common salt were mixed to a powder. 512.4 g of the former powder and 1.09 kg of the latter powder were mixed, and the powder agent for blocking nonspecific adsorption was prepared.

EXAMPLE 7

Embodiment of ELISA

A mixed solution 50 μl of anti-human κ and anti-human λIgG (prepared by Tago Company) which was diluted to 1,000 times with 0.05M sodium bicarbonate was pipetted in each well of a ELISA plate having 96 wells (produced by Sumitomo Bakelite Company), and the plate was allowed to stand overnight at 4° C. The next morning, the antibody solution was discarded, and an agent for blocking nonspecific adsorption was injected into each well and left for one hour. After each well was washed with a solution for blocking nonspecific adsorption for two times, each 50 μl of human serum IgG (prepared by Midori Juji Company) having concentrations of 0-1000 ng/ml was added and left for one hour. After each well was washed with the above solution for six times, ABTS was added and the absorbance was determined at 405 nm.

In order to block the plates, the following agents were used.

(1) A solution obtained by diluting 1% SMP/0.1M citric acid (pH 6.2) shown in Example 1 with deionized water to four times.

(2) A solution obtained by dissolving 0.7 g of the powder prepared in Example 5 in 100 ml of deionized water, pH 6.2.

(3) A solution obtained by dissolving one g of the powder prepared in Example 6 in 100 ml of deionized water, pH6.3.

(4) A solution dissolving 1% BSA in a buffer of phosphoric acid containing 0.15 mole of common salt, pH7.2 (PBS).

The following agents were used for diluting the samples.

(1) A solution obtained by diluting 1% SMP/0.1M citric acid (pH 6.2) shown in Example 1 with deionized water to ten times.

(2) A solution obtained by dissolving 0.3 g of the powder prepared in Example 5 in 100 ml of deionized water.

(3) A solution obtained by dissolving 0.4 g of the powder prepared in Example 6 in 100 ml of deionized water.

(4) 0.1% BSA/PBS

The following agents were used for washing the plates.

(1) A solution obtained by diluting 1% SMP/0.1M citric acid (pH 6.2) shown in Example 1 with deionized water to ten times.

(2) A solution containing 0.02% Tween 20 and 0.3 g of the powder prepared in Example 5 in 100 ml of deionized water.

(3) A solution containing 0.02% Tween 20 and 0.4 g of the powder prepared in Example 6 in 100 ml of deionized water.

(4) A solution containing 0.02% Tween 20.

Figure 2:
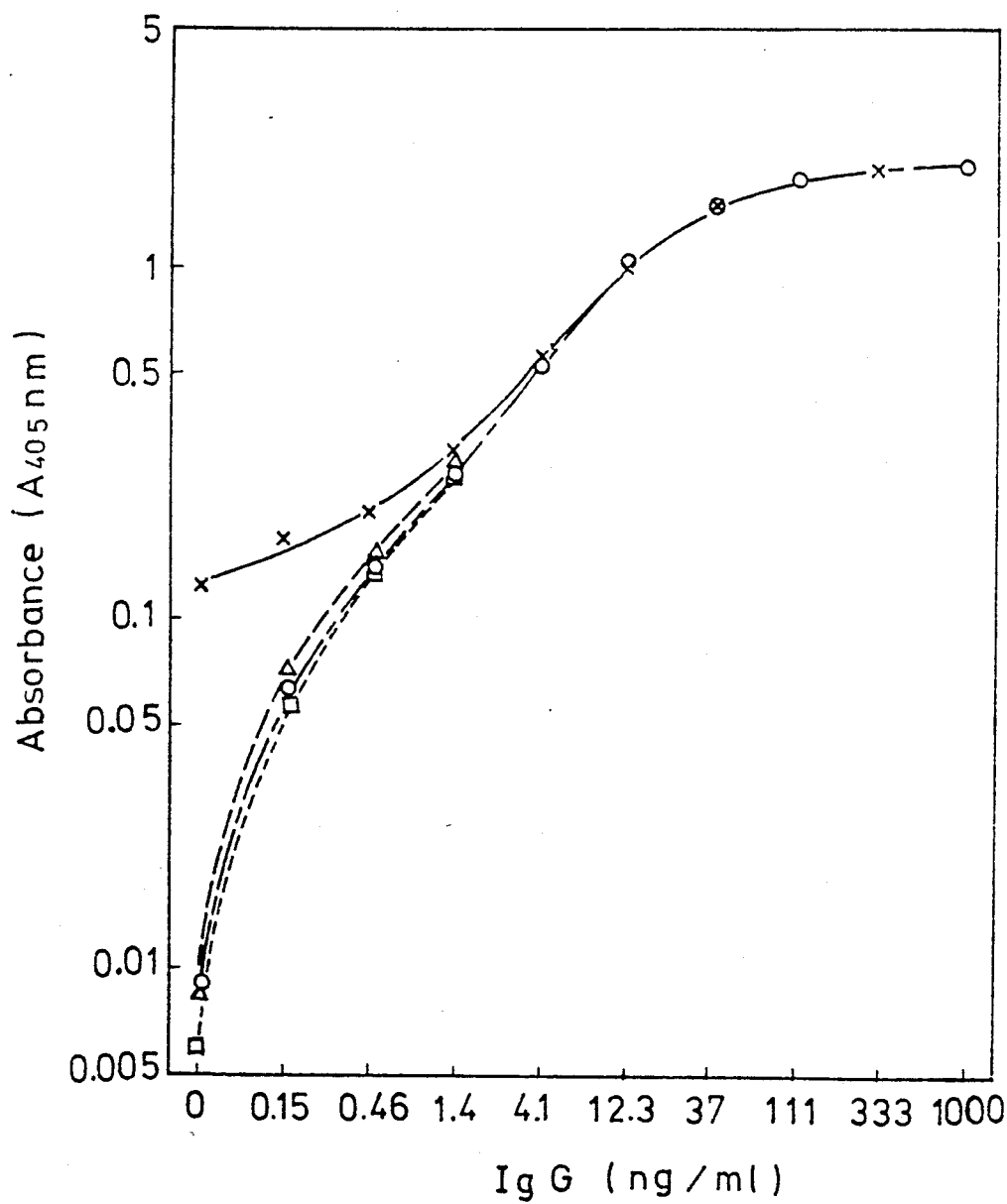
FIG. 2 is a graph showing the relation of concentration of human IgG and absorbance in Example 7. The blocking, diluting and washing conditions of the plates are shown by a circle in the case of (1), a triangle in the case of (2), a square in the case of (3), and a cross in the case of (4).

The results are shown in FIG. 2. When BSA is used, the absorbance is especially high on the side of low concentration, and it shows that the nonspecific adsorption blocking is not sufficient. However, when the powders prepared in Examples 5 and 6 are dissolved, the same blocking effect is observed as in the solution obtained by diluting 1% SMP/0.1M citric acid (pH 6.2) shown in Example 1 with deionized water.

TABLE 4

| The influence of the organic acid concentration on the absorbance of ELISA | |
| --- | --- |
| Concentration of organic acids | OD 405 nm |
| A | 0.19 ± 0.01 |
| B | 0.58 ± 0.01 |

A. A sample (human IgG 100 ng/ml, peroxidase-bound anti-human IgG antibody) was blocked with a solution in which the spray-dried powder of non fat dry milk-citric acid-sodium hydroxide in Example 6 was dissolved in milk concentration of 0.4% (4 mM citric acid), and diluted with a solution in which the same powder was dissolved in an amount of 0.1% by weight (1 mM citric acid).

B. The sample was blocked with a solution in which the same powder was dissolved in milk concentration of 0.4% (40 mM citric acid), and diluted with a solution in which the same powder was dissolved in an amount of 0.1% by weight (10 mM citric acid).

We claim:

1. An agent for blocking nonspecific adsorption, comprising a combination of milk protein as an effective constituent and a buffer solution containing one or more principal constituents selected from the group comprising organic acids and their salts, wherein the ratio of milk solid concentration(%)/organic acid concentration (mM) is 0.1 and less.

2. An agent for blocking nonspecific adsorption as claimed in claim 1 in which the agent is liquid.

3. An agent for blocking nonspecific adsorption as claimed in claim 1 in which the agent is powder.

4. A process for production of a sterilizing agent for blocking nonspecific adsorption containing milk protein as an effective constituent, comprising the steps of combining the milk protein and a buffer solution containing one or more principal constituents selected from the group comprising organic acids and their salts, wherein the ratio of milk solid concentration(%)/organic acid concentration (mM) is 0.1 and less.

5. A process for production as claimed in claim 4 in which the pH of the buffer solution is 5.3–7.0.

6. A process for preparing a powder agent for blocking nonspecific adsorption, in which the agent contains a combination of milk protein as an effective constituent and a buffer solution containing one or more principal constituents selected from the group of organic acids and their salts, in which a solution (A) which dissolves 10–40% of milk raw materials containing the milk protein as the effective constituent in the buffer solution containing 0.1–0.3 mole of one or more principal constituents selected from the group of organic acids and their salts is dried to powder, and a buffer solution (B) which contains one or more principal constituents selected from the group of organic acids and their salts is dried to powder, respectively, and the A powder and the B powder are mixed.

7. A process for preparing as claimed in claim 6 in which 0.1–10% of the mixture of the A powder and the B powder is dissolved in water, and the pH value of the obtained solution is 5.3–7.0.

8. A process for preparing as claimed in claim 6 in which the mixture ratio of the A powder and the B powder in water is represented by the following formula: milk solid concentration (%)/concentration converted in terms of organic acid(mM)$\leq$0.1 (in the formula, the concentration converted in terms of organic acid$\leq$500 mM).

9. A method of blocking nonspecific adsorption, comprising the step of using a solution which contains a combination of milk protein as an effective constituent and a buffer solution containing one or more principal constituents selected from the group comprising organic acids and their salts, wherein the ratio of milk solid concentration(%)/organic acid concentration (mM) is 0.1 and less.

* * * * *